United States Patent
Kitakawa et al.

(10) Patent No.: US 12,275,754 B2
(45) Date of Patent: *Apr. 15, 2025

(54) PROCESS FOR PRODUCING SUGAR FATTY ACID ESTER USING ANION EXCHANGER AS CATALYST

(71) Applicant: TOHOKU UNIVERSITY, Miyagi (JP)

(72) Inventors: Naomi Kitakawa, Miyagi (JP); Tomone Sasayama, Miyagi (JP); Yuto Kamikanda, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 196 days.

This patent is subject to a terminal disclaimer.

(21) Appl. No.: 16/327,009

(22) PCT Filed: Jan. 16, 2017

(86) PCT No.: PCT/JP2017/029937
§ 371 (c)(1),
(2) Date: Feb. 21, 2019

(87) PCT Pub. No.: WO2018/038103
PCT Pub. Date: Mar. 1, 2018

(65) Prior Publication Data
US 2019/0185504 A1    Jun. 20, 2019

(30) Foreign Application Priority Data

Aug. 22, 2016 (JP) .................. 2016-162015

(51) Int. Cl.
| | | |
|---|---|---|
| *C07H 13/06* | (2006.01) | |
| *B01J 31/08* | (2006.01) | |
| *B01J 41/05* | (2017.01) | |
| *C07H 1/00* | (2006.01) | |

(52) U.S. Cl.
CPC .............. *C07H 13/06* (2013.01); *B01J 41/05* (2017.01); *C07H 1/00* (2013.01); *B01J 31/08* (2013.01); *B01J 2231/49* (2013.01)

(58) Field of Classification Search
CPC ....... B01J 41/05; B01J 41/00–18; C07H 3/04; C07H 1/00–1/08
See application file for complete search history.

(56) References Cited

U.S. PATENT DOCUMENTS

| 4,966,966 A | 10/1990 | Wada et al. |
| 2019/0185504 A1 | 6/2019 | Kitakawa et al. |

FOREIGN PATENT DOCUMENTS

| EP | 0 507 323 | 10/1992 |
| FR | 1.365.067 | 6/1964 |
| GB | 1050452 | 12/1966 |
| JP | 63-179884 | 7/1988 |
| JP | 5-148285 | 6/1993 |
| JP | 6-122694 | 5/1994 |
| JP | 2006-104316 | 4/2006 |
| JP | 2008-37847 | 2/2008 |
| JP | 2010-37256 | 2/2010 |
| JP | 2015-151400 | 8/2015 |
| WO | 2018/038103 | 3/2018 |

OTHER PUBLICATIONS

Shibasaki-Kitakawa, N. et al., Bioresource Technology, "Biodiesel production using anionic ion-exchange resin as heterogenous catalyst", 2007, vol. 98, pp. 416-421 (Year: 2007).*
International Search Report issued Sep. 26, 2017 in International Application No. PCT/JP2017/029937.
Szeja W. et al., "Otrzymywanie Estrow Sacharozy I Kwasow Tluszczowych", Zeszyty Naukowe Politechniki Slaskiej, Chemia, 1969, No. 50, p. 105-6.
International Search Report issued Oct. 29, 2019 in International (PCT) Application No. PCT/JP2019/031715.
Office Action issued Mar. 15, 2022 in U.S. Appl. No. 17/265,666.
Office Action issued Nov. 2, 2021 in U.S. Appl. No. 17/265,666.
G. Eggleston, et al., "Degradation of Sucrose, Glucose and Fructose in Concentrated Aqueous Solutions Under Constant pH Conditions at Elevated Temperature", Journal of Carbohydrate Chemistry, 2000, vol. 19, Issue 9, pp. 1305-1318, Abstract.

* cited by examiner

*Primary Examiner* — Bahar Craigo
(74) *Attorney, Agent, or Firm* — Wenderoth, Lind & Ponack, L.L.P (57) ABSTRACT

An object of the present invention is to solve the various problems with the conventional process for producing a sugar fatty acid ester, such as a sucrose fatty acid ester (FASuc), and to provide a process which has advantages such as no production of a soap by-product and ease of separation between the catalyst and the product and also enables efficient synthesis by a simple operation under mild conditions in a flow system, and to provide a composition including the sugar fatty acid ester. The present invention is directed to a process for producing a sugar fatty acid ester by a transesterification reaction of a fatty acid ester and a saccharide using an anion exchanger as a catalyst, and to a composition including such a sugar fatty acid ester.

11 Claims, 2 Drawing Sheets

PROCESS FOR PRODUCING SUGAR FATTY ACID ESTER USING ANION EXCHANGER AS CATALYST

TECHNICAL FIELD

The present invention relates to a process for producing a sugar fatty acid ester using an anion exchanger as a catalyst, and so on. Specifically, the present invention relates to a process for producing a sugar fatty acid ester by a transesterification reaction of a fatty acid ester and a saccharide using a strongly basic anion-exchange resin as a catalyst, and so on.

BACKGROUND ART

About 180 million tons of sucrose (Suc), a sugar, is estimated to be produced annually. As a single organic compound, sucrose has the largest class of production scale, and high purity sucrose products are inexpensively available. Therefore, various methods of using sucrose as a chemical raw material have been proposed. Currently, a sucrose fatty acid ester (FASuc) is one of sucrose derivatives industrially produced.

FASuc is a nonionic surfactant having Suc as a hydrophilic group and a fatty acid (FA) as a lipophilic group wherein the Suc and the FA derived from a vegetable oil are ester-bonded to each other. The FASuc can be changed to be hydrophilic or lipophilic by controlling the number of fatty acids bonded to the eight hydroxyl groups of sucrose, and therefore has a wide range of hydrophile-lipophile balance (HLB) values. The FASuc has not only an emulsifying action but also high functional properties including solubilizing ability, dispersing ability, and lubricating ability.

Further, recently, in the pharmaceutical field, studies are made on the use of FASuc as a binder for tablet, and the utilization of FASuc in the medicine field is also expected.

FASuc is a biomass-derived chemical product of a high value added, which is produced from inexpensive sugar and vegetable oil, but it has been known that the miscibility of Suc which is hydrophilic and a fatty acid is so poor that synthesis of FASuc is difficult.

In the conventional industrial production process, FASuc is produced by transesterification reaction of Suc and a fatty acid methyl ester (FAMe) using dimethyl sulfoxide (DMSO) as an amphiphilic solvent, and using $Na_2CO_3$ as a homogeneous alkali catalyst.

However, the above-mentioned reaction has problems in that reduced pressure conditions for removing by-produced methanol (MeOH) are essential to increase the conversion, in that a soap is by-produced due to a reaction of FAMe and a catalyst, in that the homogeneous catalyst is difficult to separate, and in that a continuous operation is impossible, and these problems cause the cost to be increased.

For solving the problems, for example, a method has been proposed in which a reactor having a packed column and a plurality of condensers arranged in series is used and the condensate in the first stage condenser is refluxed into the column top of the packed column (PTL 1).

As another industrial process for producing a FASuc, an attempt has been made to conduct transesterification without using an organic solvent and a catalyst (PTL's 2 and 3). For example, PTL 3 has a description of a method in which a sugar fatty acid ester as an emulsifying agent is added to an aqueous sucrose solution and a fatty acid methyl ester, and the resultant mixture is irradiated with ultrasonic waves and microwaves to form an emulsion, promoting the reaction.

Meanwhile, one of the present inventors, et al. have disclosed a process for producing a fatty acid ester by a transesterification reaction of a fat or oil and an alcohol, wherein an anion exchanger is used as a catalyst, and the molar ratio of the fat or oil and the alcohol is 1/30 to 1/1 (PTL 4).

Further, as a method for producing a sucrose fatty acid ester, a method has been disclosed in which sucrose and a lower alkanol ester of a fatty acid or a glyceride are caused to undergo a transesterification reaction in the presence of a cation-exchange resin which is ion-exchanged with an alkali metal (PTL 5). However, there is a description that when the reaction was performed using a basic anion-exchange resin having a quaternary ammonium group as a functional group or a basic anion-exchange resin having a tertiary amine as a functional group, satisfactory results were not obtained (page 4, left-hand upper column of PTL 5).

CITATION LIST

Patent Literature

PTL 1: JP-A-6-122694
PTL 2: JP-A-2010-37256
PTL 3: JP-A-2015-151400
PTL 4: JP-A-2006-104316
PTL 5: JP-A-63-179884

SUMMARY OF INVENTION

Technical Problem

An object of the present invention is to solve the above various problems with the conventional process for producing a sugar fatty acid ester, such as a sucrose fatty acid ester (FASuc), and to provide a process which has advantages such as no production of a soap by-product and ease of separation between the catalyst and the product and also enables efficient synthesis by a simple operation under mild conditions, preferably in a flow system.

Solution to Problem

The present inventors have found that the above-mentioned problems can be solved by using an anion exchanger as a catalyst, and completed the present invention.

Specifically, the present invention is directed to the following aspects.

[Aspect 1]
A process for producing a sugar fatty acid ester, including performing a transesterification reaction of a fatty acid ester and a saccharide using an anion exchanger as a catalyst.

[Aspect 2]
The process according to aspect 1, wherein the saccharide is pre-adsorbed on the anion exchanger prior to the transesterification reaction.

[Aspect 3]
The process according to aspect 2, which includes the steps of: adsorbing the saccharide on the anion exchanger and then synthesizing the sugar fatty acid ester using the anion exchanger on which the saccharide has been adsorbed in the adsorbing step.

[Aspect 4]
The process according to aspect 3, wherein the adsorbing step includes feeding a reaction solution containing the saccharide to the anion exchanger to adsorb the saccharide on the anion exchanger.

[Aspect 5]

The process according to aspect 3 or 4, wherein the synthesizing step includes feeding a reaction solution containing the fatty acid ester to the anion exchanger on which the saccharide has been adsorbed in the adsorbing step to synthesize the sugar fatty acid ester.

[Aspect 6]

The process according to aspect 5, wherein the reaction solution containing the fatty acid ester further contains the saccharide.

[Aspect 7]

The process according to aspect 6, wherein the reaction solution used in the synthesizing step has a molar concentration ratio of the fatty acid ester to the saccharide of 1:0.5 to 1:5.

[Aspect 8]

The process according to any one of aspects 1 to 7, wherein the anion exchanger is a strongly basic anion-exchange resin.

[Aspect 9]

The process according to any one of aspects 1 to 8, wherein the fatty acid ester is an ester of a fatty acid having 1 to 30 carbon atoms and a lower alcohol having 1 to 8 carbon atoms.

[Aspect 10]

The process according to any one of aspects 1 to 9, wherein the saccharide is at least one selected from the group consisting of a monosaccharide, a disaccharide, and a polysaccharide.

[Aspect 11]

The process according to any one of aspects 1 to 8, wherein the fatty acid ester is methyl oleate, and the saccharide is sucrose.

[Aspect 12]

A composition including a sugar fatty acid ester produced by the process according to any one of aspects 1 to 11.

[Aspect 13]

The composition according to aspect 12, wherein a mono-fatty acid ester makes up 80% by mass or more of the sugar fatty acid ester.

Advantageous Effects of Invention

By the process of the invention, the above-mentioned problems of the conventional process are solved, and a sugar fatty acid ester can be obtained in high yield by a simple operation under mild conditions. Further, with respect to the sugar fatty acid ester obtained as a product, a conventional process for producing a sugar fatty acid ester has a problem in that a fatty acid ester is used in such a large amount that a di- or tri-fatty acid ester having a plurality of fatty acids added to one sugar is inevitably formed. In contrast, the process of the invention has an advantage in that almost all the produced sugar fatty acid ester, for example, 80% by mass or more, preferably 95% by mass or more of the sugar fatty acid ester is a mono-fatty acid ester.

BRIEF DESCRIPTION OF DRAWINGS

FIG. 2-1 is a graph showing the results in Example 6.

FIG. 2-2 is a graph showing the results in Example 7.

FIG. 2-3 is a graph showing the results in Example 8.

DESCRIPTION OF EMBODIMENTS

The present invention is directed to a process for producing a sugar fatty acid ester using a transesterification reaction of a fatty acid ester and a saccharide, characterized in that the process uses an anion exchanger as a catalyst.

With respect to the anion exchanger, for example, there can be used an anion-exchange resin known to those skilled in the art, preferably a strongly basic anion-exchange resin which is an anion exchanger that has a quaternary ammonium group having a tertiary amine chemically bonded to an insoluble carrier. Such a strongly basic anion-exchange resin has, for example, pKa>11, preferably pKa>13 for a functional group.

Examples of the strongly basic anion-exchange resins include Diaion PA-306 (manufactured by Mitsubishi Chemical Corporation), Diaion PA-306S (manufactured by Mitsubishi Chemical Corporation), Diaion PA-308 (manufactured by Mitsubishi Chemical Corporation), Diaion HPA-25 (manufactured by Mitsubishi Chemical Corporation), and Dowex 1-X2 (manufactured by Dow Chemical Company).

The strongly basic anion-exchange resin is in a chloride form just after being purchased, and therefore is regenerated to be in a hydroxide form before used in the invention. For example, as a regenerating agent, a 0.5 to 2 mol/dm$^3$ sodium hydroxide solution is used, and the flow rate of the regenerating agent passing through the resin is preferably about 2 to 10 mL-NaOH/minute per 1 mL of the anion-exchange resin. The amount of the flowing regenerating agent used is 5 to 20 mL per 1 mL of the anion-exchange resin. After completion of the regeneration, the anion-exchange resin is satisfactorily washed so that the regenerating agent does not remain, and is finally swelled with a solvent to be used in the reaction, and then can be used in the invention.

When the anion-exchange resin is classified according to the degree of crosslinking or porosity, there can be mentioned those of a gel type, a porous type, or a highly porous type. Examples of functional groups for strongly basic anion-exchange resin include a trimethylamine group, a dimethylethanolammonium group, an N-alkyl-N,N-dialkanolamine group, and a trialkanolamine group.

Further, in the anion exchanger, as an insoluble carrier, ones having resin skeletons of various chemical structures can be used. Specific examples include synthetic polymers, such as polystyrene crosslinked by divinylbenzene or the like, polyacrylic acid, a crosslinked poly(meth)acrylate, and a phenolic resin, and crosslinked products of polysaccharide naturally produced, such as cellulose. Of these, synthetic polymers are preferred, and crosslinked polystyrene is further preferred. The degree of crosslinking varies depending on the amount of the divinylbenzene used, based on the total amount of the monomers, and, for example, is selected from the range of from 1 to 10% by mass. In this case, the lower the degree of crosslinking, the more likely the reactant having a larger molecular size diffuses into the inside of the polymer, but the functional group concentration is reduced, and hence there is present an optimum value of the degree of crosslinking for achieving high catalytic activity for the transesterification reaction.

The fatty acid ester and saccharide used in the process of the invention as reactants (raw materials to be fed) can be selected from arbitrary compounds known to those skilled in the art according to the type or purpose of the use of the sugar fatty acid ester which is an intended product of the process of the invention. Further, these compounds can be prepared by an arbitrary method known to those skilled in the art, or commercially available various types of fatty acid esters and saccharides can be used.

For example, the fatty acid ester to be used may be a fatty acid ester of a lower alcohol having a linear or branched chain hydrocarbon skeleton of 1 to 8 carbon atoms, preferably 1 to 5 carbon atoms, and a fatty acid having 1 to 30 carbon atoms, such as lauric acid, myristic acid, palmitic acid, stearic acid, oleic acid, behenic acid, or erucic acid.

Further, as the saccharide, one or more saccharides selected from monosaccharides, disaccharides, such as sucrose, and polysaccharides can be used.

Therefore, as a specific example of the fatty acid ester used in the process of the invention, there can be mentioned methyl oleate used in the below-described Examples, and, as a specific example of the saccharide, there can be mentioned sucrose.

In the process of the invention, the fatty acid ester which is lipophilic and the saccharide which is hydrophilic are totally different in polarity and unlikely to be miscible with each other, and therefore, for example, they can be reacted with an anion exchanger in a system of a solvent having amphiphilicity known to those skilled in the art, such as dimethyl sulfoxide, dimethylformamide, ethyl methyl ketone, ethyl acetate, 2-propanol, propylene glycol, methanol, ethanol, or 2-methyl-1-propanol.

As shown in the Examples below, it has been found that, when a fatty acid ester is in contact with the OH group as an active site of an anion exchanger in a state such that a saccharide in a satisfactory amount is not present, the anion exchanger loses the catalytic activity due to an ion-exchange reaction between the fatty acid residue of the fatty acid ester and the OH group of the anion exchanger, so that a transesterification reaction is not efficiently caused between the saccharide then incorporated into the anion exchanger and the fatty acid ester.

Such a reaction did not occur in a technique for continuously synthesizing a fatty acid ester using, as a catalyst, an anion exchanger uniquely developed by one of the present inventors, et al. (PTL 4), and hence was a problem unexpected from the prior art.

In the process of the invention, for solving such a technical problem, an anion exchanger on which a saccharide is substantially preliminarily adsorbed is preferably used. For example, the process is preferably performed using two stages including a saccharide adsorption step (first step), which is a step of adsorbing a saccharide on an anion exchanger prior to a transesterification reaction of a fatty acid ester and the saccharide, and then a sugar fatty acid ester synthesis step (second step), which is a step of performing a transesterification reaction of a fatty acid ester and the saccharide using the anion exchanger obtained in the first step.

In the process of the invention, in each stage, with respect to the contacting method for the reactants and the anion exchanger, the contacting can be made by an arbitrary method known to those skilled in the art, such as a batch method (batch system) or a continuous method (flow system). With respect to the form of the apparatus, examples include an apparatus provided with a treatment vessel, and an apparatus which transfers a resin in a circulation system or a countercurrent system. Examples of contacting methods include flowing (method of allowing a reactant to flow through an ion-exchange resin packed bed), stirring (method using a stirring vessel), fluidizing (fluidized bed reactor), and shaking (shaking type reactor). An apparatus of a column flowing type in which the introduction inlet for a raw material to be fed and the recovery inlet for a product are fixed, an apparatus of an expanded bed (expanded bed column) type, or an apparatus of a batch type can be used.

In a batch system, as the reaction proceeds, the reactant concentration is reduced. Therefore, when it is difficult to maintain high saccharide concentration, the reactant can be added to the system if necessary. On the other hand, in a continuous method (flow system) using a reactor packed with a resin, an intended sugar ester synthesis reaction can be advantageously preferentially advanced by maintaining high saccharide concentration.

When the process of the invention is performed using the above-mentioned continuous method (flow system), it is preferred that, as a first step, a reaction solution containing a saccharide is fed to an anion exchanger to perform an adsorption step for the saccharide, and then, as a second step, a reaction solution containing only a fatty acid ester or containing a fatty acid ester and a saccharide is fed to the anion exchanger to cause a transesterification reaction between them, performing a synthesis step for a sugar fatty acid ester. Particularly, it is preferred that the reaction solution containing the fatty acid ester and saccharide is fed so that the saccharide in the anion exchanger which is a catalyst is maintained at a high concentration during the second step, and the saccharide concentration of the reaction solution is increased.

With respect to the concentration of the saccharide used in the second step (synthesis step), for example, the molar concentration ratio of the saccharide to the fatty acid ester in the reaction solution is preferably in the range of from 1:0.5 to 1:5, more preferably in the range of from 1:0.5 to 1:3. When the concentration ratio of the saccharide is less than 0.5, as mentioned above, it is likely that the anion exchanger loses the catalytic activity, so that a transesterification reaction is not efficiently caused between the saccharide then incorporated into the anion exchanger and the fatty acid ester. On the other hand, when the concentration ratio of the saccharide is more than 5, the concentration of the reaction solution becomes too high, and the cost is increased and this is disadvantageous in view of the productivity. Further, when an excess saccharide is added, an operation for removing the saccharide from the product is needed, causing the productivity to be poor.

In the process of the invention, for achieving a desired aim, the operations of the above-mentioned two steps and an arbitrary production process may be used in combination. For example, the process of the invention can further comprise a step of separating a sugar fatty acid ester which is an intended product from an alcohol which is another product and other impurities and the like to purify the product. Specifically, in the process of the invention for producing a sugar fatty acid ester using an anion exchanger as a catalyst, the composition obtained after performing a transesterification reaction of a fatty acid ester and a saccharide is a composition containing in a solvent a sugar fatty acid ester which is a product and the saccharide and fatty acid ester which are unreacted reactants, or the composition further containing an alcohol and the like, and, for purifying the sugar fatty acid ester which is a product from the composition, an extraction step and a water washing step are performed repeatedly desired times, the extraction solvent is distilled off from the extractant, and then drying is performed so that a mixture containing a solvent-free product is obtained. From the mixture containing the product, a sugar fatty acid ester having a high purity can be obtained by using arbitrary means or methods known to those skilled in the art, for example, a distillation step, a membrane separation step, a preparative liquid chromatography separation step, and the like in combination.

Further, the composition obtained by the process of the invention contains unreacted reactants in addition to the sugar fatty acid ester as mentioned above. The purity of the sugar fatty acid ester in the composition, in terms of a molar fraction, is less than 100%, and may be preferably in the range of from 0.01 to 99%, more preferably in the range of from 0.1 to 90%, and may be in the range of from 1 to 70%, and, for increasing the purity to a desired purity, the composition can be further subjected to known treatment for increasing the purity. Further, it is preferred that 80% by mass or more, preferably 90 to 99.9% by mass of the sugar fatty acid ester contained in the composition is a mono-fatty acid ester. These individual components of the composition can be analyzed by a known analysis apparatus, such as liquid chromatography.

Further, when the process of the invention is performed in a flow system, by using the anion-exchange resin in the form of a packed bed, the anion-exchange resin can be repeatedly utilized in the same reaction, but the resin is preferably appropriately regenerated. In this case, the regeneration treatment is performed according to a known method. For example, the anion-exchange resin is treated with an acid solution using a solvent having miscibility with a free fatty acid to replace the functional group by an acid group, and then the resultant resin is treated with an alkali solution to replace the functional group by an OH group, followed by swelling with the reaction solvent. The aim of the regeneration treatment is to replace the functional group of the resin by a catalytically active (OH) group, but the functional group of the resin is possibly in a fatty acid form, and, when the resin is directly treated with an alkali solution, a soap is formed to hamper the replacement of the functional group. The treatment of the resin with an acid solution is needed to avoid the formation of a soap and the like and to achieve efficient replacement of the functional group by an OH group. As the acid, an organic acid, such as formic acid, acetic acid, or citric acid, can be used.

The other conditions and means in the process of the invention, for example, the molar concentrations and molar ratios of the individual reactants, the amount of the anion exchanger used, the amount ratio of the anion exchanger and the reactants, the temperature and pressure for the reaction system, the reaction time and the like can be appropriately selected from arbitrary ones known to those skilled in the art, taking into consideration the types of the reactants and anion exchanger used and the like. For example, the reaction time for each step can be appropriately set by those skilled in the art according to the reaction temperature, the amount of the anion exchanger used, or the like. The reaction is performed generally at 20 to 100° C., preferably at 30 to 70° C. With respect to the reaction pressure, there is no particular limitation. It is easy to conduct the reaction under atmospheric pressure from an operational point of view, but, if necessary, the reaction pressure may be increased to about 1 to 10 atm., or may be reduced to about 0.002 to 1 atm.

The present invention is also directed to an apparatus for performing the above-described process, for example, a reaction apparatus comprising one or a plurality of vessels (reactors) packed with a predetermined anion exchanger, each having an introduction inlet for a reactant on one side and a recovery inlet for a product on the other side. The apparatus may have the vessel or vessels in an independent form, but may have a structure in which a plurality of the vessels are connected in parallel and/or in series. Further, with respect to the form of the vessel, there is no particular limitation, but, generally, a column is used. When a column packed with the anion-exchange resin is used, a mode using an expanded bed column packed bed having a high void ratio is preferred for preventing the resin from swelling to break the column. The expanded bed column indicates, for example, a column which is used in a separation and purification method in which an intended component dissolved is adsorbed onto adsorbent particles from a fluid having high viscosity or a fluid containing solids so that the component is recovered, and which is operated by column chromatography in a state such that the fluid is caused to flow upwardly inside the column and the adsorbent particles having a large specific gravity are suspended in a static state to maintain a large void ratio, and, for example, a known method described in Kagaku kogaku ronbunshu, Vol. 27, No. 2 (2001), pages 145 to 148, or the like can be used. Accordingly, the present invention is also directed to the apparatus for performing the process of the invention. In the process of the invention, for example, when a solution having a density of more than 1 or a solution having high viscosity is used as a reaction solution, for preventing a bias flow to efficiently advance the reaction, an upward flow is preferably used.

Hereinbelow, the present invention will be described in detail with reference to the following Examples, which should not be construed as limiting the technical scope of the invention. In the following Examples, experiments were performed in accordance with a general method known to those skilled in the art unless otherwise specified.

Example 1

Synthesis of a Sugar Fatty Acid Ester in a Batch System
[Methods and Conditions for Experiments]

With respect to the reactants, methyl oleate (OAMe) was used as a fatty acid ester, and sucrose (Suc) was used as a saccharide. Therefore, in the present experiment, sucrose oleate (OASuc) is formed according to the reaction formula (1).

[Chem. 1]

OAMe

+

Dimethyl sulfoxide (DMSO) was used as a solvent. As a resin catalyst, a commercially available porous, strongly basic anion-exchange resin Diaion PA306S (manufactured by Mitsubishi Chemical Corporation) was used.

The anion-exchange resin has a functional group of an inactive Cl type and is in the state of being swelled with water just after shipped from the factory. Therefore, the anion-exchange resin must be subjected to activating treatment for changing the functional group from the inactive Cl type to an active OH type and for swelling the resin with a solvent. This treatment was performed in accordance with the regeneration treatment method already established by the present inventors for repeatedly utilizing a resin.

In each experiment, Suc and OAMe were individually weighed so that the respective concentrations shown in Table 1 below were achieved, and dissolved in DMSO by shaking in a constant temperature bath at 60° C. Then, the resin catalyst was added so that the amount of the resin catalyst became 20% by mass, in terms of a wet weight, based on the mass of the reaction solution, and a reaction was performed at the same temperature for 24 hours while well shaking. In this case, to study the effect of the adsorption of reactants on the resin, an experiment was performed in which one of the reactants was first adsorbed on the resin and then another one was added for a reaction, and another experiment was performed in which two reactants were simultaneously added for a reaction.

Examples 1 to 3 were performed under conditions where Suc was first adsorbed at 0.1 to 0.3 mol/dm$^3$ on the resin catalyst. Example 4 was performed under conditions where OAMe was first adsorbed at 0.1 mol/dm$^3$ on the resin catalyst. Example 5 was performed under conditions where the two reactants were simultaneously added to the resin catalyst (that is, the process of first adsorbing any one of Suc and OAMe on the resin catalyst was not performed). An experiment for comparison (Comparative Example 1) was also performed in which, instead of the resin catalyst, 2.2% by mass of a conventional homogeneous catalyst $Na_2CO_3$ was added under conditions where the two reactants were simultaneously added. The conditions for these experiments are shown in Table 1.

In each experiment, a small amount of the reaction solution was taken at intervals of a predetermined period of time, and concentrations of products, such as OASuc, were measured using a liquid chromatography having an evaporative light scattering detector.

[Results]

Figure 1:
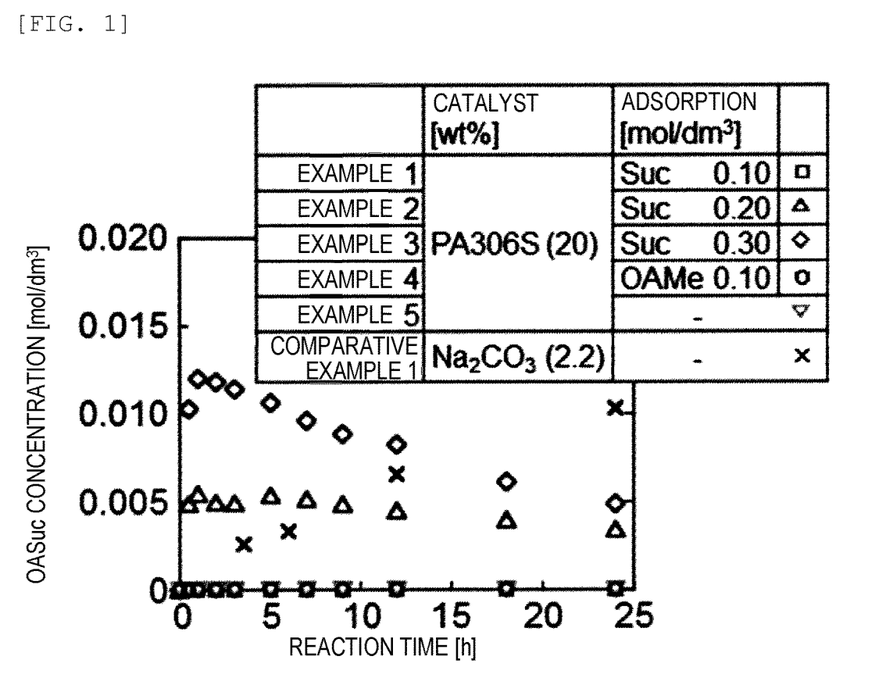
FIG. 1 is a graph showing the experimental results in Examples 1 to 5 and Comparative Example 1.

The experimental results in Examples 1 to 5 and Comparative Example 1 are shown in FIG. 1. Further, with respect to the products in Examples 1 to 5 and Comparative Example 1, the maximum OASuc concentration, the reaction time at which the maximum OASuc concentration has been achieved, and the maximum OASuc yield at that time are shown in Table 1. In Example 4 in which OAMe was first adsorbed on the resin catalyst and in Example 5 in which the two reactants were simultaneously added without an adsorption operation, the product concentration was at or below the detection limit, that is, almost no product was formed, even after the reaction for 24 hours. In contrast to Examples 4 and 5, the product was detected in Examples 1 to 3 in which Suc was first adsorbed on the resin catalyst. In Examples 1 to 3, the product OASuc concentration increased depending on the concentration of Suc adsorbed first on the resin catalyst. Particularly, in Example 3, 3 hours after the start of the reaction, the product OASuc concentration became the maximum, and the OASuc yield at that time (maximum OASuc yield) was 12%, which is equivalent to or more than the yield (10%) obtained after the reaction for 24 hours in Comparative Example 1 in which a conventional homogeneous alkali catalyst was used. From this, it has been found that, when Suc at a high concentration is first added to the resin catalyst, the formation of OASuc in high yield is observed, and that the formation rate is larger than that in the case using a homogeneous catalyst. From the fact that the OASuc concentration is reduced on the late stage of the reaction, there is a possibility that a decomposition reaction of OASuc proceeds. Therefore, it is considered that an appropriate reaction time for making the product OASuc concentration maximum is present. Further, 95% by mass or more of the obtained OASuc was a mono-fatty acid ester.

The OASuc yield is defined as "(OASuc concentration/charged OAMe concentration)×100".

TABLE 1

|  | Example 1 | Example 2 | Example 3 | Example 4 | Example 5 | Comparative Example 1 |
| --- | --- | --- | --- | --- | --- | --- |
| Catalyst | PA306S | PA306S | PA306S | PA306S | PA306S | $Na_2CO_3$ |
| Catalyst amount [wt %] | 20 | 20 | 20 | 20 | 20 | 2.2 |
| Suc Concentration [mol/dm$^3$] | 0.10 | 0.20 | 0.30 | 0.10 | 0.10 | 0.10 |
| OAMe Concentration [mol/dm$^3$] | 0.10 | 0.10 | 0.10 | 0.10 | 0.10 | 0.10 |
| Adsorption time [h] | 0.5 | 0.5 | 0.5 | 0.5 | — | — |
| Maximum OASuc concentration [mol/dm$^3$] | 0.00062 | 0.0055 | 0.012 | Not detected | Not detected | 0.010 |

TABLE 1-continued

|  | Example 1 | Example 2 | Example 3 | Example 4 | Example 5 | Comparative Example 1 |
|---|---|---|---|---|---|---|
| Reaction time [h] at which maximum OASuc concentration has been achieved | 24 | 1.5 | 3 | Not detected | Not detected | 24 |
| Maximum OASuc yield [%] | 0.62 | 5.4 | 12 | 0 | 0 | 10 |

Synthesis of a Sugar Fatty Acid Ester in a Flow System

[Methods and Conditions for Experiments]

The reaction system was changed from the above-mentioned batch system to a flow system (continuous system), and the reactants, the solvent, and amount of the resin catalyst were the same as those in Example 3. The experimental apparatus used comprises a reaction solution tank, a feed pump, a constant-temperature jacketed column-type reactor, and a constant temperature bath. The feed solution tank was placed in the constant temperature bath and maintained at 60° C. The column was packed with 22 g (wet weight) of the resin catalyst. Then, an activating treatment for the resin catalyst was performed in accordance with the same procedure as in the batch system.

Figure 21:
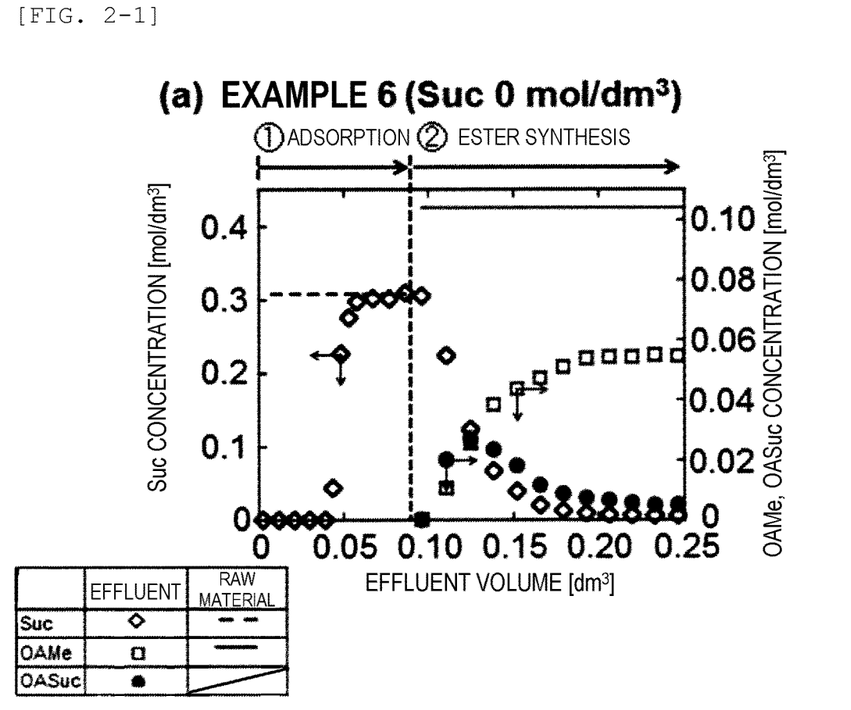
Figure 22:
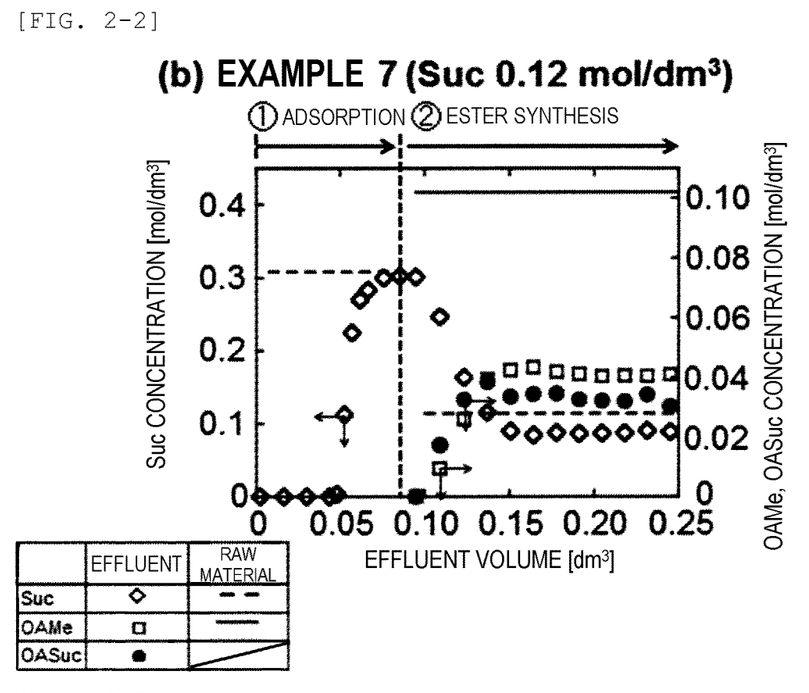
Figure 23:
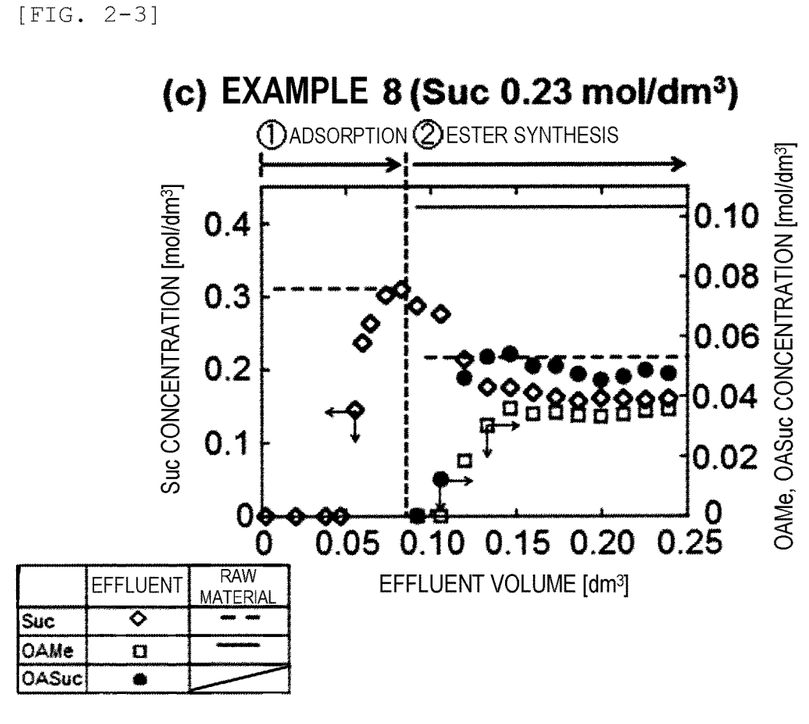

The experiment in the flow system was performed using a two-step process including an operation for adsorbing the sugar onto the resin catalyst and an operation for ester synthesis. First, in the adsorption operation, a DMSO solution of Suc at a predetermined concentration was fed using a pump in an upward flow from the bottom portion of the resin catalyst packed column maintained at 60° C. toward the upper portion and allowed to flow until breakthrough so that Suc was adsorbed on the anion-exchange resin. In this process, the Suc concentration was 0.3 mol/dm$^3$ which is the same as in Example 3, and the feed rate was 1.0 cm$^3$/min. In the synthesis operation, a DMSO solution containing only OAMe at the same concentration (0.1 mol/dm$^3$) as in Examples 1 to 5 was fed at 0.2 cm$^3$/min similarly from the bottom portion of the column (Example 6). A residence time at this flow rate in the resin packed bed was calculated. As a result, the residence time was found to be 1.5 hours. As another synthesis operation, experiments were performed in which a DMSO solution containing both OAMe at the same concentration (0.1 mol/dm$^3$) as in Examples 1 to 5 and Suc at a predetermined concentration (0.12 or 0.23 mol/dm$^3$) was similarly fed (Examples 7 and 8). The conditions for these experiments are shown in FIGS. 2-1 to 2-3 and Table 2.

TABLE 2

|  | Example 6 | Example 7 | Example 8 |
|---|---|---|---|
| Adsorption step |  |  |  |
| Suc Concentration [mol/dm$^3$] | 0.30 | 0.30 | 0.30 |
| Flow rate [cm$^3$/min] | 1.0 | 1.0 | 1.0 |
| Synthesis (reaction) step |  |  |  |
| Suc Concentration [mol/dm$^3$] | 0 | 0.12 | 0.23 |
| OAME Concentration [mol/dm$^3$] | 0.10 | 0.10 | 0.10 |
| Flow rate [cm$^3$/min] | 0.20 | 0.20 | 0.20 |
| Residence time [h] | 1.5 | 1.5 | 1.5 |
| OASuc Concentration [mol/dm$^3$] | 0.026 (max) | 0.033 | 0.051 |
| OASuc Yield [%] | 26 | 32 | 51 |

[Results]

In Example 6 in which only OAMe was fed in the synthesis step, the Suc concentration of the effluent was gradually reduced from the saturated concentration, and meanwhile, the product OASuc concentration was once increased and became the maximum, and then was gradually reduced. The obtained maximum value of the OASuc concentration and the OASuc-based yield at that value are shown in Table 2. Further, in Examples 7 and 8 in which both OAMe and Suc were fed in the synthesis step, a tendency was shown such that the OASuc concentration of the effluent was gradually increased and then became constant. The obtained constant concentration and the yield at that value are shown in Table 2.

Particularly, in Example 8, at a time when the concentration of OASuc which is a product in the effluent became constant, the OASuc concentration was 0.051 mol/dm$^3$, the concentration of Suc which is a reactant in the effluent was 0.19 mol/dm$^3$, and the OAMe concentration was 0.031 mol/dm$^3$, and, from this, the OASuc concentration of the effluent was 18.8% (molar fraction), based on the total mol (0.272 mol/dm$^3$) of the reactant and the product. When the OASuc yield is determined based on 0.1 mol/dm$^3$ which is the charged OAMe concentration, the yield is 51%. Under the above conditions, at a point in time when the yield is 100%, the OASuc concentration of the effluent in terms of a molar fraction is 36.8%. As apparent from this, by maintaining the high Suc concentration in the column, an efficient FASuc synthesis was able to be achieved with a residence time as short as 1.5 hours. Further, 95% by mass or more of the obtained OASuc was a mono-fatty acid ester.

The above-mentioned results have confirmed that, by the process of the invention, a FASuc synthesis can be achieved at a yield of 51%, which is even more efficient than a conventional method, under mild conditions at a reaction temperature of 60° C. and under atmospheric pressure.

INDUSTRIAL APPLICABILITY

The present invention provides new potential in the development of a method for synthesizing a sugar fatty acid ester having various uses, such as a sucrose fatty acid ester.

The invention claimed is:

1. A process for producing a sugar fatty acid ester, comprising steps of:
   adsorbing a saccharide on an anion exchanger by feeding a reaction solution containing the saccharide to the anion exchanger to adsorb the saccharide on the anion exchanger; and
   performing a transesterification reaction of a fatty acid ester and the saccharide using the anion exchanger as a catalyst by feeding a reaction solution containing the fatty acid ester to the anion exchanger after the adsorbing step to synthesize the sugar fatty acid ester,
   wherein the saccharide is pre-adsorbed on the anion exchanger in the adsorbing step prior to the step of performing the transesterification reaction, and
   the anion exchanger is a strongly basic anion-exchange resin.

2. The process according to claim 1, wherein the reaction solution containing the fatty acid ester used in the performing step further contains a saccharide that is the same saccharide adsorbed on the anion exchanger in the absorbing step.

3. The process according to claim 2, wherein the reaction solution used in the performing step has a molar concentration ratio of the fatty acid ester to the saccharide of 1:0.5 to 1:5.

4. The process according to claim 1, wherein the fatty acid ester is an ester of a fatty acid having 1 to 30 carbon atoms and a lower alcohol having 1 to 8 carbon atoms.

5. The process according to claim 1, wherein the saccharide is at least one selected from the group consisting of a monosaccharide, a disaccharide, and a polysaccharide.

6. The process according to claim 1, wherein the fatty acid ester is methyl oleate, and the saccharide is sucrose.

7. The process according to claim 6, wherein the reaction solution used in the performing step has a molar concentration ratio of methyl oleate to sucrose of 1:1 to 1:3.

8. The process according to claim 6, wherein the reaction solution used in the performing step has a molar concentration ratio of methyl oleate to sucrose of 1:1.

9. The process according to claim 1, wherein the anion exchanger is a porous type strongly basic anion-exchange resin.

10. The process according to claim 1, wherein 80% by mass or more of the sugar fatty acid ester obtained after the performing step is a mono-fatty acid ester.

11. The process according to claim 1, wherein 90 to 99.9% by mass or more of the sugar fatty acid ester obtained after the performing step is a mono-fatty acid ester.

* * * * *

UNITED STATES PATENT AND TRADEMARK OFFICE
CERTIFICATE OF CORRECTION

PATENT NO. : 12,275,754 B2  
APPLICATION NO. : 16/327009  
DATED : April 15, 2025  
INVENTOR(S) : Naomi Kitakawa et al.

Page 1 of 1

It is certified that error appears in the above-identified patent and that said Letters Patent is hereby corrected as shown below:

On the Title Page

In item (22), "Jan. 16, 2017", should read --August 22, 2017--.

Signed and Sealed this
Twenty-fourth Day of June, 2025

Coke Morgan Stewart
*Acting Director of the United States Patent and Trademark Office*